United States Patent
Davidov et al.

(10) Patent No.: US 6,712,609 B2
(45) Date of Patent: Mar. 30, 2004

(54) SUPPORTING STRUCTURE FOR A DENTAL MODEL AND A METHOD FOR FORMING THEREOF

(76) Inventors: Evgeny Davidov, 84-20 Austin St., Apt. 3F, Kew Gardens, NY (US) 11415; Vyacheslav Iskhakbayev, 83-60 118th St., Apt. 1B, Kew Gardens, NY (US) 11415

( * ) Notice: Subject to any disclaimer, the term of this patent is extended or adjusted under 35 U.S.C. 154(b) by 0 days.

(21) Appl. No.: 10/103,046

(22) Filed: Mar. 22, 2002

(65) Prior Publication Data

US 2003/0180682 A1 Sep. 25, 2003

(51) Int. Cl.⁷ ................................................. A61C 11/00
(52) U.S. Cl. ........................................ 433/60; 433/213
(58) Field of Search ............................ 433/53, 54, 60, 433/34, 213, 74

(56) References Cited

U.S. PATENT DOCUMENTS

| | | | |
|---|---|---|---|
| 4,265,619 A | * 5/1981 | Lucki et al. | 433/54 |
| 4,319,875 A | * 3/1982 | Beckwith | 433/60 |
| 4,337,039 A | 6/1982 | Martin | |
| 4,382,787 A | 5/1983 | Huffman | |
| 4,496,320 A | * 1/1985 | Hwang et al. | 433/60 |
| 4,608,016 A | 8/1986 | Zeiser | |
| 4,842,242 A | 6/1989 | Huffman | |
| 4,854,868 A | * 8/1989 | Pitre | 433/60 |
| 5,106,296 A | 4/1992 | Varde | |
| 5,506,095 A | * 4/1996 | Callne | 433/60 |
| 5,678,992 A | * 10/1997 | Carlson | 433/60 |
| 5,716,209 A | 2/1998 | Faierstain | |
| 5,800,166 A | 9/1998 | Huffman | |
| 5,868,569 A | 2/1999 | Huffman | |
| 6,019,601 A | 2/2000 | Cho | |
| 6,210,160 B1 | 4/2001 | Shima | |
| 6,247,927 B1 | 6/2001 | Walter | |

FOREIGN PATENT DOCUMENTS

| | | | |
|---|---|---|---|
| DE | 2923208 | * 12/1980 | 433/60 |
| FR | 2590475 | * 5/1987 | 433/60 |

* cited by examiner

*Primary Examiner*—Cary E. O'Connor
(74) *Attorney, Agent, or Firm*—I. Zborovsky

(57) ABSTRACT

The invention is a supporting structure for a dental model in a dental articulator. The supporting structure includes an articulator plate and a base of the dental model. The base of the dental is provided with at least one cavity extending internally into the base from its bottom surface. The shape of the cavity is determined by the mold forming the base. In one embodiment, the cavity has straight walls. In another embodiment, the cavity is barrel-shaped. The articulator plate is provided with an alignment structure, which may include a pair of straight-walled projections, for use in combination with the straight-walled cavity, or a pair of curved springs, for use in combination with barrel-shaped cavity. The articulator plate is secured to the base by inserting and retaining the alignment structure inside the provided cavities. The articulator plate is provided with a shaft for attaching the dental model to a dental articulator.

7 Claims, 2 Drawing Sheets

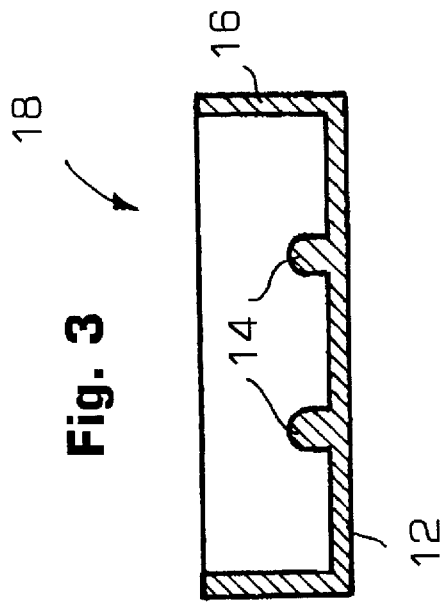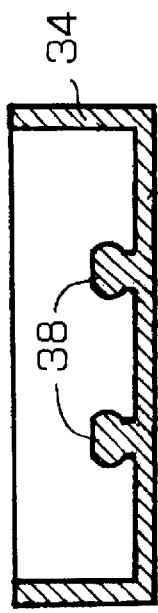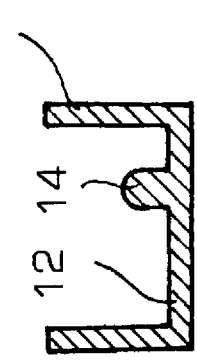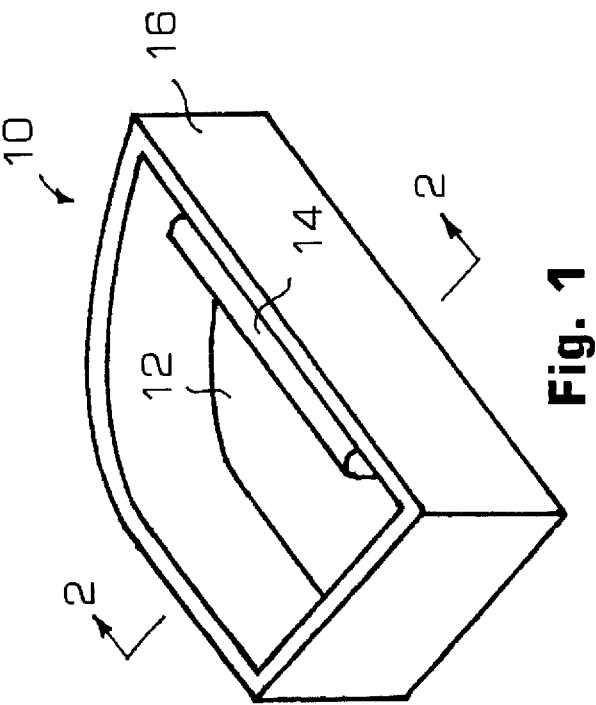

SUPPORTING STRUCTURE FOR A DENTAL MODEL AND A METHOD FOR FORMING THEREOF

FIELD OF THE INVENTION

The present invention relates to dental models used in dental articulators, more particularly, it relates to a structure supporting the dental model in the articulator and a method for forming and supporting the dental model.

BACKGROUND OF THE INVENTION

To accurately form and position false teeth or caps, a dentist normally makes a negative impression of the affected tooth or teeth. The negative impression may be partial, unilateral or bilateral, depending upon the extent of work to be done; the negative impression serves as a mold for developing a die of the patient's tooth or teeth. The negative impression is obtained by partially filling a tray with thermoplastic material. The filled tray is inserted within the patient's mouth such that the teeth and adjacent gum sink into and create a cavity within the thermoplastic material. Shortly thereafter, the thermoplastic material will cure and retain an exact impression of the patient's teeth and adjacent gum. This is an essentially standard technique presently used by most dentists.

To form a tooth die, a pourable casting stone, known as pink stone is poured into the negative impression up to at least the margin or base of the tooth. The pink stone is compacted to preclude voids and remove any air bubbles. After the pink stone is at least partially cured, wax or similar lubricant is swathed upon the surface of the pink stone.

In the prior art, the base for the dental mold is made by one of two methods. First, additional pourable hardenable stone, generally referred to as yellow stone, is poured within the negative impression to cover the pink stone and the retainer with sufficient depth of yellow stone to form a solid base. After both the pink stone and the yellow stone have hardened, the tray and supported thermoplastic material is peeled away to leave a conventional dental model. Alternatively, a patty of yellow stone is formed upon a glass or other smooth surface. The partially or completely cured pink stone is placed thereupon.

In either method, pins are lodged or fixated in the pink stone to extend into and slidably engage the yellow stone. Usually, three pins per model tooth to be worked on are used. The pins serve the function of maintaining registration of the model tooth with respect to the remaining die.

Either of the above processes for making the bases of dental models tends to result in each base being somewhat unique and individualized. When the dental models are placed upon a dental articulator to perform work on the dental model, a substantial amount of time and expertise is necessary to properly attach and align the upper and lower co-acting dental models to reproduce the relationship of the patient's jaws. The requisite time for aligning the dental models is exacerbated by the non-uniformity of the dental model base configurations and thicknesses and requires yet further time and effort to positionally orient and attach each base upon its respective arm of the articulator.

The dental base described and illustrated in U.S. Pat. No. 4,378,929 is formed by pouring the yellow stone into a mold. The mold standardizes the width, breath, height and configuration of the base. Such standardization permits the use of indexing means in the bases to mount opposing bases of a dental model upon an articulator. Additionally, there is described and illustrated the use of an overhang for forcing a depression in the surface of the base to which the tooth die is attached, which depression delineates a platform. The tooth die (pink stone) is attached upon the platform. To sever a model tooth from the tooth die, mesial and distal saw cuts are made through the tooth die to a point just below the line of demarcation between the tooth die and the base. The line of demarcation is coincident with the surface of the platform. As the saw blade need not be angled to have the saw end clear the opposing quadrant of the tooth die, the depth of cut into the base may be minimized at a point just below the platform surface.

In U.S. Pat. No. 4,382,787, there is described an articulator attachable to opposed pairs of dental model bases through a mounting means. The articulator is particularly easily usable with size standardized bases for dental models of the type described in U.S. Pat. No. 4,378,929. One embodiment of the mounting means usable as part of the articulator includes a tab, tang or ridge for penetrable engagement with a slot formed in the rear sidewall of a dental model base.

U.S. Pat. No. 4,842,242 discloses a standard sized base for a full or quadrant dental model and having a slot formed in the rear sidewall of the base, which slot is enhanced for adhesive engagement with an arm of an articulator.

SUMMARY OF THE INVENTION

It is an object of the present invention to provide a dental model having a base immovably supporting the dental model in a dental articulator.

It is another object of the present invention to provide a supporting plate for supporting the dental model with the provided base in a dental articulator.

It is a further object of the present invention to provide means for aligning the supporting plate of the articulator with the dental model having the provided base.

The invention provides a supporting structure for supporting a dental model in a dental articulator. The supporting structure includes an articulator plate and a base of the dental model. The base of the dental model is provided with at least one cavity extending internally into the base from its bottom surface. The shape of the cavity is determined by the mold forming the base. In one embodiment, the cavity has straight walls. In another embodiment, the cavity is barrel-shaped. The articulator plate is provided with an alignment structure, which may include a pair of straight-walled projections, for use in combination with the straight-walled cavity, or a pair of curved springs, for use in combination with barrel-shaped cavity. The articulator plate is secured to the base by inserting and retaining the alignment structure inside the provided cavities. The articulator plate is provided with a shaft for attaching the dental model to a dental articulator.

The above and other objects, aspects, features and advantages of the invention will be more readily apparent from the description of the preferred embodiments thereof taken in conjunction with the accompanying drawings and appended claims.

BRIEF DESCRIPTION OF THE DRAWINGS

The invention is illustrated by way of example and not limitation and the figures of the accompanying drawings in which like references denote like or corresponding parts, and in which:

FIG. 1 is an isometric view of the half-mold for forming a lower left quadrant base for a dental model.

FIG. 2 is a cross section of the half-mold shown in FIG. 1 taken along the line 2—2.

FIG. 3 is a cross-section of a full mold having two elongated straight-walled projections for creating two corresponding cavities in the formed base.

FIG. 4 is a cross-sectional view of a full mold having two elongated barrel-shaped projections for creating two corresponding cavities in the formed base.

DETAILED DESCRIPTION OF THE PREFERRED EMBODIMENTS AND THE DRAWINGS

Figure 6:
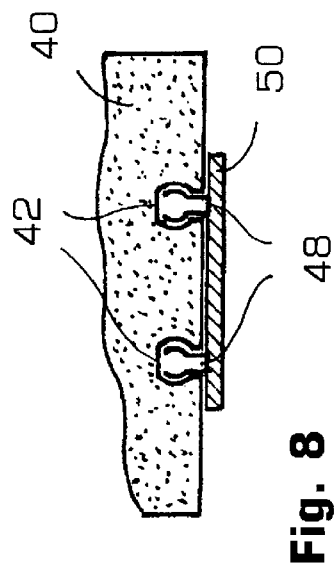
FIG. 6 is a cross-sectional view of the plate shown in FIG. 5 with the base of a dental model placed on top of the articulator plate, where the elongated straight-walled projections of the plate are fit tightly inside their corresponding elongated straight-walled cavities of the base.

Referring to FIG. 1, there is shown a half-mold 10 for forming a lower left quadrant base for a dental model. The half-mold 10 preferably has a bottom 12 fully surrounded by a side wall 16. The half-mold 10 is preferably made of resin and can be optionally made flexible. An elongated projection 14 extends vertically from the bottom 12. As shown in FIG. 2, the elongated projection 14 has straight walls and a slightly convex top edge. The top edge of the elongated projection 14 is substantially parallel to the bottom 12. When yellow stone (or any other suitable material) is poured into the half-mold 10, the elongated straight-walled projection 14 forms an elongated straight-walled cavity 24 (a pair of which is shown in FIG. 6) in the resulting base of a dental model.

Similarly to the half-mold 10, the full mold 18, cross-section of which is shown in FIG. 3, is preferably made of resin and has the bottom 12 surrounded by the side-wall 16. To ensure proper alignment of the resulting base, however, the full mold 18 is provided with two elongated straight-walled projections 14. When yellow stone (or any other suitable material) is poured into the full mold 18, two elongated straight-walled projections 14 form two elongated straight-walled cavities 24 in the resulting base 20 of a dental model, as shown in FIG. 6.

Figure 5:
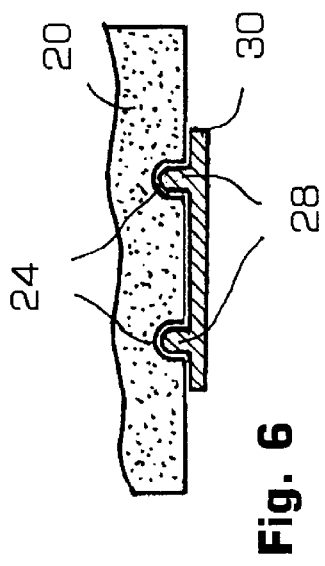
FIG. 5 is an articulator plate having two elongated straight-walled projections for supporting the base having two corresponding straight-walled cavities.

In accordance with the preferred embodiment of the present invention, a supporting articulator plate 30, preferably made of metal, is provided, as shown in FIG. 5. The supporting articulator plate 30 preferably has a tray 22 with an extending rectangular shaft 26 insertable into an arm of a dental articulator (not shown). Two elongated projections 28 extend vertically from the tray 22. As shown in FIG. 5, each elongated projection 28 has straight walls, a slightly convex top edge, and is substantially conforming to the shape and size of the elongated projection 14. Thus, elongated straight-walled projections 28 are configured to be insertable into the elongated straight-walled cavities 24 of the base 20 with a tight fit, as shown in FIG. 6, to preserve an alignment between the dental model having the base 20 and the plate 30 during manipulations of the dental articulator.

In accordance with the preferred embodiment, to form a dental model, a technician will first prepare a tooth die using the described pink stone technique or any other conventionally known technique. The base 20 is then formed by pouring yellow stone (or any other suitable material) into the provided half-mold 10 (or full mold 18). The partially or completely cured pink stone is then pressed into a partially cured base 20 to allow them to cure together, thereby forming the dental model to be used in a dental articulator. As described above, the mold is provided with elongated straight-walled projections 14, which form corresponding straight-walled cavities 24 within the base 20. When the dental model is completely cured, it is removed from the mold and is placed upon the supporting articulator plate 30 such that elongated straight-walled projections 28 of the plate 30 are tightly fit inside elongated straight-walled cavities 24 of the base 20. Projections 28 and cavities 24 insure a proper alignment and frictional immobility between the dental model and the supporting articulator plate 30 during manipulations of the dental articulator and allow for repeated removal of the dental model from the articulator if needed.

Figure 7:
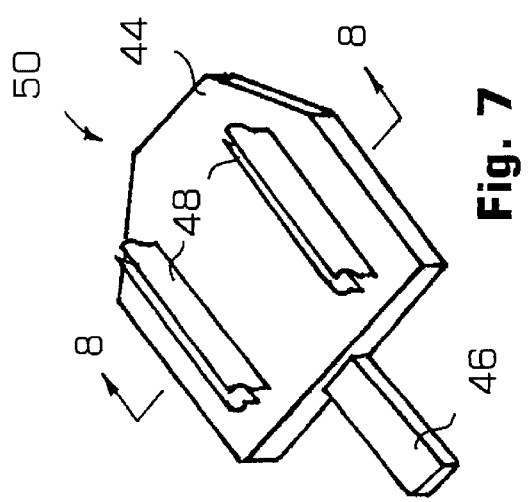
FIG. 7 is an articulator plate having two elongated curved springs for supporting a dental model having the base with two barrel-shaped cavities.
Figure 8:
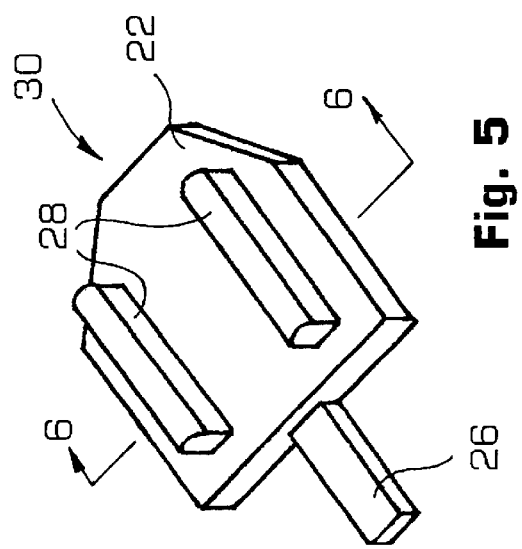
FIG. 8 is a cross-sectional view of the plate shown in FIG. 7 with the base of a dental model placed on top of the plate, where the elongated curved springs of the articulator plate are pushed into and biased against the walls of their corresponding barrel-shaped cavities of the base.

An alternative embodiment of the present invention is illustrated in FIGS. 4, and 7-8. Referring to FIG. 4, there is shown a full mold 32 for forming a base for a dental model. The full mold 32 preferably has a bottom 36 fully surrounded by a side wall 34. The full mold 32 is preferably made of semi-flexible resin. Two elongated projections 38 extend vertically from the bottom 36. As shown in FIG. 4, each elongated projection 38 has a barrel shape and a straight top edge. The top edge of the elongated barrel-shaped projection 38 is substantially parallel to the bottom 36. When yellow stone (or any other suitable material) is poured into the mold 32, elongated barrel-shaped projections 38 form elongated barrel-shaped cavities 42 in the resulting base 40 of a dental model, as shown in FIG. 8.

In accordance with the alternative embodiment of the present invention, a supporting articulator plate 50, preferably made of metal, is provided, as shown in FIG. 7. The supporting articulator plate 50 preferably has a tray 44 with an extending rectangular shaft 46 insertable into an arm of a dental articulator (not shown). Two elongated springs 48 extend vertically from the tray 44. As shown in FIG. 7, each elongated spring 48 has curved walls and is substantially conforming to an outer shape and size of the elongated barrel-shaped projections 38. Thus, elongated curved springs 48 are configured to be insertable into and snap-fit within elongated barrel-shaped cavities 42 of the base 40, as shown in FIG. 8, to preserve an alignment between the dental model having the base 40 and the plate 50 during manipulations of the dental articulator.

In accordance with the alternative embodiment of the present invention, to form a dental model, a technician will first prepare a tooth die using the described pink stone technique or any other conventionally known technique. The base 40 is then formed by pouring yellow stone (or any other suitable material) into the provided mold 32. The partially or completely cured pink stone is then pressed into a partially cured base 40 to allow them to cure together, thereby forming the dental model to be used in a dental articulator. As described above, the mold is provided with elongated barrel-shaped projections 38, which form corresponding barrel-shaped cavities 42 within the base 40. When the dental model is completely cured, it is removed from the mold and is placed upon the supporting articulator plate 50 such that elongated curved springs 48 of the plate 50 are pushed into and biased against the walls of their corresponding elongated barrel-shaped cavities 42 of the base 40. Biased springs 48 and cavities 42 insure a proper alignment and immobility between the dental model and the supporting articulator plate 50 during manipulations of the dental articulator. At the same time, repeated removal and placement of the dental model onto the tray are possible.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A supporting structure for supporting a dental model in an articulator, comprising:

an articulator plate having a top surface; said articulator plate made from a non-deformable material and a base of said dental model, said base having a bottom surface being in opposing relationship with said top surface of said articulator plate; said base made from a single non-deformable material, wherein said base further comprises at least one elongated cavity vertically extending internally into said base from said bottom surface and wherein said articulator plate further comprises at least one elongated alignment means comprising an elongated projection extending perpendicularly to said top surface of said articulator plate said alignment means being insertable into said cavity until frictional immobility and having an outer shape substantially conforming to an inner shape of said cavity.

2. The supporting structure of claim 1, wherein said elongated projection has straight walls.

3. The supporting structure of claim 1, wherein said cavity has straight walls.

4. A dental model comprising:

a base having a top surface, a bottom surface and at least one elongated cavity vertically extending from said bottom surface, said cavity comprises an elongated inner shape, said base made from a single non-deformable material;

a tooth die secured to said top surface of said base; and a plate made from a non-deformable material and having at least one elongated attachment means comprising an elongated projection extending vertically from said plate, said means having an outer shape complementing said inner shape of said elongated cavity of said base, said means adapted to be inserted into said elongated cavity until frictional immobility, wherein
   said plate is attachable to a dental articulator and wherein said attachment means and said cavity are configured to substantially immovably secure said plate to said bottom surface of said base.

5. The dental model of claim 4, wherein said attachment means comprises an elongated straight-walled projection extending vertically from said plate.

6. The dental model of claim 5, wherein said cavity has straight walls.

7. A method of forming a dental model, comprising the steps of:

forming a tooth die;

molding a base of said dental model from a single non-deformable material, said molding further comprising forming a top surface, a bottom surface and at least one elongated cavity vertically extending from said bottom surface;

securing said tooth die to said top surface of said base; and securing an articulator plate having at least one attachment means to said bottom surface of said base, said securing further comprising inserting said attachment means into said cavity of said base and substantially immovably retaining said attachment means within said cavity.

* * * * *